United States Patent [19]

Kuwada et al.

[11] 4,145,418
[45] Mar. 20, 1979

[54] THIENOPYRIDINE SUBSTITUTED CEPHALOSPORINS

[75] Inventors: Yutaka Kuwada, Ashiya; Kanji Meguro, Takarazuka, both of Japan

[73] Assignee: Takeda Chemical Industries, Ltd., Japan

[21] Appl. No.: 755,428

[22] Filed: Dec. 29, 1976

[30] Foreign Application Priority Data

Jan. 6, 1976 [JP] Japan .................................. 51-1315
Mar. 29, 1976 [JP] Japan .................................. 51-34971

[51] Int. Cl.$^2$ .................. A61K 31/545; C07D 501/36
[52] U.S. Cl. .............................. 424/246; 260/239.1; 546/114; 546/80; 424/271; 544/25; 544/27; 544/28
[58] Field of Search .................... 260/243 C; 424/246; 544/27

[56] References Cited

U.S. PATENT DOCUMENTS

| | | | |
|---|---|---|---|
| 3,134,774 | 5/1964 | Chow et al. | 260/243 C |
| 3,487,074 | 12/1969 | Sheehan | 260/243 C |
| 4,041,161 | 8/1977 | Kocsis et al. | 544/22 |
| 4,061,748 | 12/1977 | Yamada et al. | 424/246 |

Primary Examiner—Nicholas S. Rizzo
Assistant Examiner—David E. Wheeler
Attorney, Agent, or Firm—Craig & Antonelli

[57] ABSTRACT

Thienopyridine derivatives of the formula:

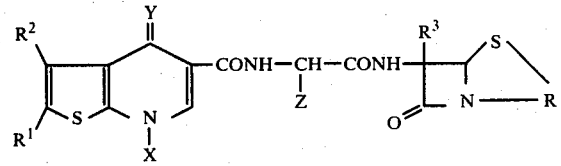

wherein $R^1$ and $R^2$ are the same or different and each is hydrogen, an alkyl, an aryl, an aralkyl or a halogen; $R^1$ and $R^2$ may, taken together, represent an alkylene group; X is hydrogen or an alkyl; Y is oxygen or sulfur; Z is phenyl which may optionally be substituted; $R^3$ is hydrogen or an alkoxy; and R is a group of the formula:

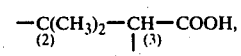

or of the formula:

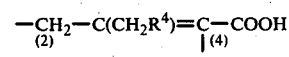

(wherein $R^4$ is hydrogen, an acyloxy or a nucleophilic compound residue) or a pharmaceutically acceptable salt thereof are found to have activity against a broad spectrum of gram-positive and gram-negative bacteria, particularly against bacteria of the genus Pseudomonas 6 Claims, No Drawings

THIENOPYRIDINE SUBSTITUTED CEPHALOSPORINS

DESCRIPTION OF THE INVENTION

This invention relates to thienopyridine derivatives having the following formula and methods for producing the same:

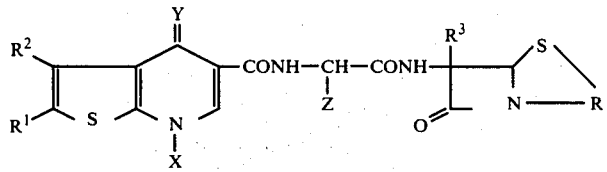

(I)

wherein $R^1$ and $R^2$ are the same or different and each is hydrogen, an alkyl, an aryl, an aralkyl or a halogen; $R^1$ and $R^2$ may, taken together, represent an alkylene group; X is hydrogen or an alkyl; Y is oxygen or sulfur; Z is phenyl which may optionally be substituted; $R^3$ is hydrogen or an alkoxy; and R is a group of the formula:

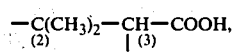

or of the formula:

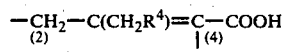

(wherein $R^4$ is hydrogen, an acyloxy or a nucleophilic compound residue), or a pharmaceutically acceptable salt thereof.

Referring to thienopyridine derivatives (I), the alkyls $R^1$, $R^2$ and X may each be methyl, ethyl, propyl, isopropyl, n-butyl, isobutyl, sec-butyl, tert-butyl, pentyl, hexyl, cyclopropylmethyl or cyclohexyl, to name but a few. Generally, use is made of straight-chain, branched or cyclic alkyl group containing 1 to 6 carbon atoms. Where $R^1$ and $R^2$, taken together, represent an alkylene group such as trimethylene or tetramethylene, they form a five- to six-membered alicyclic fused ring and said ring may include unsaturation or/and substituents such as those alkyl groups hereinbefore mentioned. The halogen $R^1$, $R^2$ may for example be chlorine, bromine, fluorine or iodine. $R^1$ and $R^2$ may also represent an aryl or aralkyl group such as phenyl, chlorophenyl, tolyl, benzyl, phenethyl, etc. As substituents on the phenyl, there may be mentioned hydroxyl, amino, nitro, and alkyl groups having 1 to 3 carbon atoms such as those hereinbefore mentioned. As the alkoxy group $R^3$, there may be mentioned, those having 1 to 3 carbon atoms, namely methoxy, ethoxy and propoxy. The acyloxy group $R^4$ may for example be acetyloxy, propionyloxy, 3-oxobutyryloxy, 3-carboxypropionyloxy, 2-carboxybenzoyloxy, 4-carboxypropionyloxy, mandelyloxy, 2-(carboethoxycarbamoyl)-benzyloxy, 2-(carboethoxysulfamoyl)benzoyloxy or 3-ethoxycarbamoylpropionyloxy. The nucleophilic compound residue may for example be a quaternary ammonium group or a mercapto group substituted by a nitrogen-containing heterocyclic group. The nitrogen-containing heterocyclic group is a five- or six-membered ring including 1 to 4 hetero-atoms selected from the group consisting of oxygen, sulfur and nitrogen and, as such, may for example be pyridyl, N-oxidepyridyl, pyrimidyl, pyridazinyl, N-oxide-pyridazinyl, pyrazolyl, imidazolyl, thiazolyl, 1.2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadizaolyl, 1,2,5-oxadiazolyl, 1,2,3-triazolyl, 1,2,4-triazolyl, 1H-tetrazolyl or 2H-tetrazolyl. Among them, thiadiazolyl groups, triazolyl groups and tetrazolyl groups are particularly preferred. These hetero-rings may carry such substituents as lower alkyl groups, e.g. methyl, ethyl, propyl, etc.; lower alkoxy groups, e.g. methoxy, ethoxy, etc.; halogens, e.g. chlorine, bromine, etc.; halogenoalkyl groups, e.g. trifluoromethyl, trichloromethyl, etc.; hydroxyl, mercapto; amino; carboxyl; carbamoyl; morpholino; sulfo; alkoxycarbonyl; mono-, di- or trialkylaminoalkyl groups, e.g. dimethylaminoethyl, etc.; mono- or dialkylcarbonylalkyl groups; alkylthioalkyl groups, e.g. methylthiomethyl, etc.; mercapto and amino groups as substituted by alkyls such as those hereinbefore mentioned. The alkyl or alkoxy in the substituent groups on the heterorings as exemplified above has carbon atoms of 1 to 3. As said quaternary ammonium group, there may be mentioned pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)-pyridinium, 4-(carboxymethyl)pyridinium, 4-(hydroxymethyl)-pyridinium, 4-(trifluoromethyl)pyridinium, quinolinium, picolinium, lutidinium, etc.

The 4-carboxyl group on the cephem ring and/or the sulfo or other acidic group in the 7-acyl moiety of these thienopyridine derivatives (I) may be either unprotected or protected in the form of a salt, i.e. the salts of non-toxic cations such as sodium, potassium, etc.; basic amino acids such as arginine, ornithine, lysine, histidine, etc.; or polyhydroxyalkylamines such as N-methylglucamine, diethanolamine, triethanolamine, trishydroxymethylaminomethane, etc.

The compounds (I) of the present invention include two typical classes of the compounds, namely:

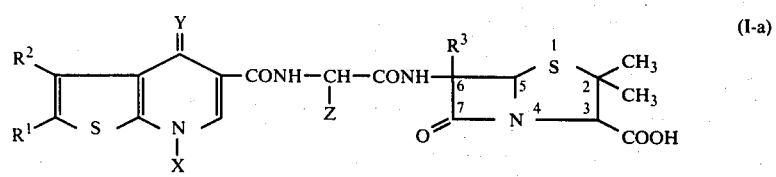

(I-a)

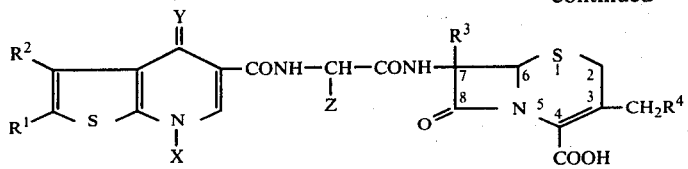

wherein all the symbols have the same meanings as defined above.

In the class of the compounds (I-a), $R^3$ is preferably hydrogen.

For illustrative purpose, typical examples of the compounds as represented by the above formulas are enumerated below:

Compound[I-a]

D-(−)-α-(7-ethyl-4, 7-dihydro-4-oxothieno[2,3-b]pyridine-5-carboxamido)benzylpenicillin and its salt;

D(−)-α-(7-ethyl-4,7-dihydro-2-methyl-4-oxothieno[2,3-b]pyridine-5-carboxamido)benzylpenicillin and its salt;

D(−)-α-(1-ethyl-1,4,5,6,7,8-hexahydro-4-oxo[I]benzothieno[2,3-b]pyridine-3-carboxamido)benzylpenicillin and its salt;

D(−)-α-(2-bromo-7-ethyl-4,7-dihydro-4-oxothieno[2,3-b]pyridine-5-carboxamido)benzylpenicillin and its salt;

D(−)-α-(2-bromo-4,7-dihydro-4-oxothieno[2,3-b]pyridine-5-carboxamido)benzylpenicillin and its salt;

D(−)-α-(2-chloro-7-ethyl-4,7-dihydro-4-oxothieno[2,3-b]pyridine-5-carboxamido)-p-hydroxybenzylpenicillin and its salt;

D(−)-α-(2-bromo-7-ethyl-4,7-dihydro-4-oxothieno[2,3-b]pyridine-5-carboxamido)-p-hydroxybenzylpenicillin and its salt;

D(−)-α-(2-bromo-7-ethyl-4,7-dihydro-3-methyl-4-oxothieno[2,3-b]pyridine-5-carboxamido)benzylpenicillin and its salt;

D(−)-α-(4-hydroxy-2-methyl-3-phenylthieno[2,3-b]pyridine-5-carboxamido)benzylpenicillin and its salt;

D(−)-α-(2-benzyl-7-ethyl-4,7-dihydro-4-oxothieno[2,3-b]pyridine-5-carboxamido)benzylpenicillin and its salt; and D(−)-α-(2-bromo-4,7-dihydro-7-methyl-4-oxothieno[2,3-b]pyridine-5-carboxamido)benzylpenicillin and its salt.

Compound[I-b]

7-[D(−)-α-(2-bromo-7-ethyl-4,7-dihydro-4-oxothieno[2,3-b]pyridine-5-carboxamido)-α-phenylacetamido]-3-(1,2,3-triazol-5-ylthiomethyl)-3-cephem-4-carboxylic acid;

7-[D(−)-α-(2-bromo-7-ethyl-4,7-dihydro-4-oxothieno[2,3-b]pyridine-5-carboxamido)-α-4-hydroxyphenylacetamido)]-3-(1,2,3-triazol-5-ylthiomethyl)-3-cephem-4-carboxylic acid;

7-[D(−)-α-(2-bromo-7-ethyl-4,7-dihydro-4-oxothieno[2,3-b]pyridine-5-carboxamido)-α-phenylacetamido]-3-(1-methyl-1H-tetrazol-5-ylthiomethyl)-3-cephem-4-carboxylic acid;

7-[D(−)-α-(2-bromo-7-ethyl-4,7-dihydro-4-oxothieno[2,3-b]pyridine-5-carboxamido)-α-phenylacetamido]-3-(1,3,4-thiadiazol-2-ylthiomethyl)-3-cephem-4-carboxylic acid;

7-[D(−)-α-(2-bromo-4,7-dihydro-7-methyl-4-oxothieno[2,3-b]pyridine-5-carboxamido)-α-phenylacetamido]-3-(1,2,3-triazol-5-ylthiomethyl)-3-cephem-4-carboxylic acid;

7-[D(−)-α-(2-bromo-4,7-dihydro-7-methyl-4-oxothieno[2,3-b]pyridine-5-carboxamido)-α-phenylacetamido]-3-(1-methyl-1H-tetrazol-5-ylthiomethyl)-3-cephem-4-carboxylic acid;

7-[D(−)-α-(2-bromo-4,7-dihydro-7-methyl-4-oxothieno[2,3-b]pyridine-5-carboxamido)-α-phenylacetamido]-3-[1-(2-dimethylaminoethyl)-1H-tetrazol-5-ylthiomethyl]-3-cephem-4-carboxylic acid;

7-[D(−)-α-(7-ethyl-4,7-dihydro-2-methyl-4-oxothieno[2,3-b]pyridine-5-carboxamido)-α-phenylacetamido]-3-(1-methyl-1H-tetrazol-5-ylthiomethyl);

7-[D(−)-α-(4,7-dihydro-2,7-dimethyl-4-oxothieno[2,3-b]pyridine-5-carboxamido)-α-phenylacetamido]-3-(1-methyl-1H-tetrazol-5-ylthiomethyl)-3-cephem-4-carboxylic acid;

7-[D(−)-α-(2-bromo-7-ethyl-4,7-dihydro-4-oxothieno[2,3-b]pyridine-5-carboxamido)-α-phenylacetamido]-3-methyl-3-cephem-4-carboxylic acid; and 7-[D(−)-α-(2-bromo-7-ethyl-4,7-dihydro-4-oxothieno[2,3-b]pyridine-5-carboxamido)-α-phenylacetamido]cephalosporanic acid These compounds (I) can be produced by reacting a compound of the formula:

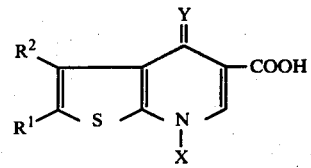

wherein all the symbols are the same as defined above, with a compound of the formula:

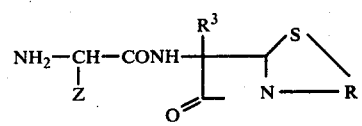

wherein all the symbols have the same meanings as defined above.

The compounds (I) can also be produced by reacting a compound of the formula:

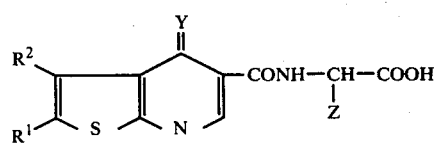

wherein all the symbols have the same meanings as defined above, with a compound of the formula:

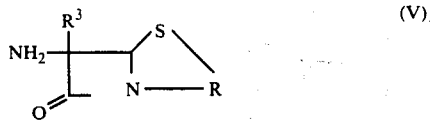

wherein all the symbols have the same meanings as defined above.

Furthermore, the compounds represented by the following formula belonging to the class of the compounds [I-b]:

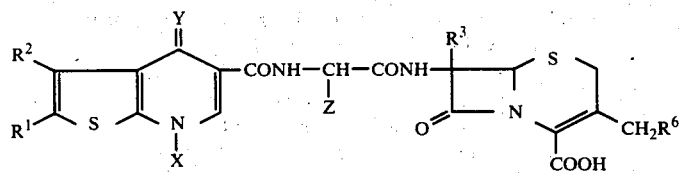

wherein $R^6$ represents a nucleophilic compound residue, can be produced by reacting a compound of the formula:

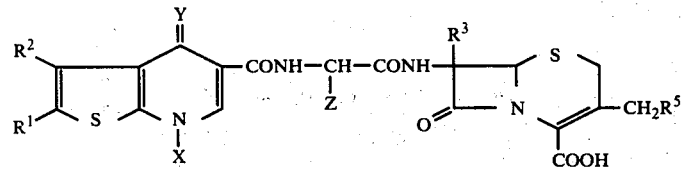

wherein $R^5$ represents halogen or an acyloxy, with a nucleophilic compound.

The halogen represented by $R^5$ may also include those as mentioned above in connection with $R^1$ and $R^2$.

In practicing the first and second processes as mentioned above, the starting material carboxylic acids (II) and (IV) may be employed either as the free acid or in the form of a reactive derivative at the carboxyl function. Thus, said acids (II), (IV) are each reacted as the free acid; as the salt of sodium, potassium, calcium, trimethylamine or pyridine, for instance; or as any of such reactive derivatives as the corresponding acid halide, acid anhydride, mixed acid anhydride, acitive amide or active ester. As examples of the active ester, there may be mentioned p-nitrophenyl ester, 2,4-dinitrophenyl ester, pentachlorophenyl ester, N-hydroxysuccinimide ester, N-hydroxyphthalimide ester, etc. As examples of said mixed acid anhydride, there may be mentioned the mixed anhydrides with carbonic acid monoesters such as carbonic acid monomethyl ester, carbonic acid monoisobutyl ester, etc.; and the mixed anhydrides with optionally-halogenated lower alkanoic acids such as pivalic acid trichloroacetic acid, etc. Where (II) or (IV) is used as the free acid or in the form of a salt, a suitable condensing agent is employed. As such condensing agent, there may be mentioned dehydrating agents such as N,N'-di-substituted carbodiimides, e.g. N,N'-dicyclohexylcarbodiimide; azolides, e.g. N,N'-carbonylimidazole, N,N'-thionyldiimidazole, etc.; phosphorus oxychloride; alkoxyacetylenes, etc. It appears that where such a condensing agent is employed, the reaction proceeds via the formation of a reactive derivative of the carboxylic acid. Where the starting compound (III) has an amino group, it is in certain cases preferable to previously protect the amino group. For this purpose, there may be employed the amino group which has been substituted by such an acyl group as may be easily removed under mild conditions (for example, under mildly acidic or alkaline conditions, under reducing conditions such as for catalytic reduction, etc.) or the amino group protonated by an acid such as hydrochloric acid, sulfuric acid, formic acid or acetic acid. Thus, the above-mentioned acyl group may include formyl, amyloxycarbonyl, t-butoxycarbonyl, 2,2,2-trichloroethoxycarbonyl, benzyloxycarbonyl, p-nitrobenzyloxycarbonyl, 2-methylsulfonylethoxycarbonyl, etc.

The 4-carboxyl group of compound (III) and of compound (V) may be one of the salts of alkali metals, alkaline earth metals or organic amines, such as sodium, potassium, magnesium, aluminum, triethylamine, etc., or of the esters which may be easily converted to a free carboxyl group by treatment with an alkali, acid or enzyme or by reduction or which will display activity in vivo, such as 2-methylsulfonylethyl, trimethylsilyl, dimethylsilenyl, benzhydryl, 2,2,2-trichloroethyl, phenacyl, p-methoxybenzyl, p-nitrobenzyl, methoxymethyl, etc.

The reactions in the first and the second processes as mentioned above may be normally conducted smoothly and with advantage in a solvent. As the solvent, there may be employed any of the common solvents or a mixture of such solvents unless they are detrimental to the present reaction, including, among others, water, acetone, diisobutyl ketone, tetrahydrofuran, ethyl acetate, dioxane, acetonitrile, chloroform, dichloromethane, dichloroethylene, pyridine, dimethylaniline, dimethylformamide, dimethylacetamide, dimethylsulfoxide, etc. While the reaction temperature is not very critical, the reaction is normally conducted under cooling or at room temperature. Where the reaction proceeds with an elimination of acid, it is conducted in the presence of a base as necessary. As the base employed for this purpose, there may be mentioned aliphatic, aromatic or heterocyclic nitrogen-containing bases, and alkali metal carbonates and bicarbonates, such as triethylamine, N,N-dimethylaniline, N-ethylmorpholine, pyridine, collidine, 2,6-lutidine, sodium carbonate, potassium carbonate, sodium hydrogen carbonate and potassium hydrogen carbonate. In certain cases, the reaction is carried out in an inert gas such as nitrogen.

The starting material carboxylic acid (IV) in the process (2) can be easily prepared by reacting a compound (II) with a compound of the formula:

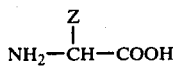

under conditions comparable to the reaction conditions described above.

According to the above third process, the compound (VI) is reacted with a nucleophilic compound. The compound (VI) may be used as the free compound or in the form of a salt of a base such as alkali metals, e.g. sodium, potassium, etc. or organic amines, e.g. trimethylamine, triethylamine, etc. Where the nucleophilic compound is a thiol, it is reacted as the free thiol or in the form of a salt at the thiol function, e.g. as the salt of an alkali metal such as lithium, sodium or potassium. This reaction is normally carried out in the neighborhood of neutrality and at room temperature or under heating at about 40° to 80° C. The reaction is conducted in a solvent which is preferably water or an aqueous solvent such as a mixture of water with a highly polar solvent inert to the reaction, such as acetone, tetrahydrofuran, dimethylformamide, methanol, ethanol or dimethylsulfoxide. Where (VI) is employed in the free form, it is sometimes preferable to add a base, e.g. sodium hydrogen carbonate or potassium carbonate, to the reaction system in order to adjust it to neutral. If necessary, a buffer solution may also be employed. While the reaction time and other conditions are desirable selected with reference to the starting material, solvent, temperature and other variables, the reaction may for example be accomplished by heating (VI) in a polar solvent (water or an aqueous organic solvent) and in the presence of one to several molar equivalents of the nucleophilic compound at room temperature to 80° C. for a few days to several hours. This reaction may be conducted in the presence of tens of molar equivalents of an inorganic salt such as KSCN or KI. As examples of said nucleophilic compound, there may be mentioned pyridine, nicotinamide, isonicotinamide, 5-mercaptotetrazole, 5-mercapto-1-methyltetrazole, 5-mercapto-2-methyltetrazole, 5-methyl-2-mercapto-1,3,4-thiazole, 5-amino-2-mercapto-1,3,4-thiadiazole, 2,5-dimercapto-1,3,4-thiadiazole, etc.

Referring to general formulas (I), (II) and (IV), where X is a hydrogen atom, these compounds have the following formulas (I'), (II') and (IV'), respectively, each representing a tautomeric form of the corresponding compound.

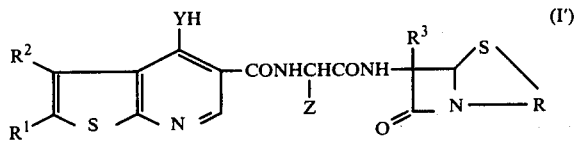

(I')

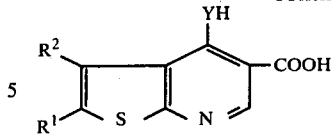

(II')

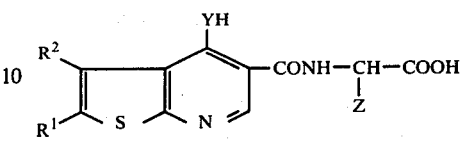

(IV')

wherein the various symbols have the same meanings as respectively defined hereinbefore.

Therefore, in preparing a reactive derivative at the carboxyl function of starting compound (II) or (IV), particularly a mixed acid anhydride of (II) or (IV), the alkoxycarbonyl chloride or acyl chloride is preferably employed in a proportion not less than 2 molar equivalents, for such activating agent will be partially consumed at the —YH function. This process gives rise to a product of the general formula (VIII):

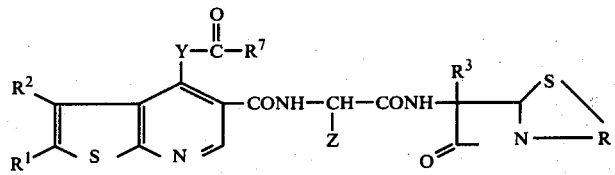

(VIII)

where $R^7$ is an alkoxy group or an alkyl group having 1 to 3 carbon atoms which may optionally be halogenated; the other symbols have the same meanings as respectively defined hereinbefore, and the desired compound (I) (X=hydrogen) can be obtained by treatment with a basic reagent, either without isolating (VIII) or after isolating the same from the reaction mixture. As examples of said basic reagent, there may be mentioned sodium carbonate, potassium carbonate, sodium hydroxide, aqueous ammonia, methylamine, dimethylamine, piperidine, morpholine, potassium acetate, sodium acetate, sodium 2-ethylhexanoate, potassium 2-ethylhexanoate, etc.

The resultant thienopyridine derivatives may, after conducting an unmasking reaction for removal of the protective group in a manner known per se if necessary, be isolated and purified by conventional procedures such as extraction with a solvent, pH adjustment, phasic transfer, distillation, crystallization, recrystallization or chromatography(on polystyrene resin, sulfonated polystyrene resin, etc.). Where the amino group in the starting material has been protected as protonated by an acid, the free amino-compound is obtained on mere pH adjustment in the purification stage. Where the amino group has been protected by an acyl group, the free amino-compound can be obtained by a conventional deacylating treatment appropriate to the particular acyl group, e.g. treatment with an acid where the acyl group is formyl, amyloxycarbonyl or t-butoxycarbonyl; reduction where the acyl group is 2,2,2-trichloroethoxycarbonyl, benzyloxycarbonyl or p-nitrobenzyloxycarbonyl; or treatment with an alkali for removal of 2-methylsulfonylethoxycarbonyl. Further, the thienopyridine derivatives (I) may be put to use as the free compound or in the form of a salt at the 3- or 4-carboxyl function, such as the salts of nontoxic cations, e.g.

sodium, potassium etc.; basic amino acids, e.g. arginine, ornithine, lysine, histidine, etc.; and polyhydroxyalkylamines, e.g. N-methylglucamine, diethanolamine, triethanolamine, trishydroxymethylaminomethane, etc.

The thienopyridine derivatives (I) of the present invention are antibiotic agents having activity against a broad spectrum of gram-positive and gram-negative bacteria, being particularly active against bacteria of the genus Pseudomonas. Improved inhibitory activity and a broadening of antimicrobial spectrum are also noted against *Escherchia coli*, *Klebsiella pneumoniae* and bacteria of the genus Proteus.

Like the known penicillins or cephalosporins, the thienopyridine derivatives (I) according to this invention are orally administered as bulk powders or, in admixture with physiologically acceptable vehicles, carriers or excipients, in such dosage forms as tablets, capsules, powders, granules, etc. They may also be formulated as solutions, suspensions, etc. for use as injections, or in admixture with ointment and other bases which are known per se, as drugs for external application. Among those thienopyridine derivatives (I), the specific compounds as set forth above, for example, are preferably administered, for example against Pseudomonas infections, at a dose level of 5 to 100 mg/Kg, preferably 5 to 50 mg/Kg, daily per adult human, in about 3 to 5 divided doses by the oral or other route. Against infections with other gram-negative or gram-positive bacteria, the same compounds may be employed just as the known penicillins or cephalosporins.

The present invention is described in further detail with reference to the following Examples, which are set forth for not limiting but illustrative purpose only.

EXAMPLE 1

D(—)-α-(7-ethyl-4,7-dihydro-4-oxothieno[2,3-b]pyridine-5-carboxamido)benzylpenicillin A mixture of 223 mg of 7-ethyl-4,7-dihydro-4-oxothieno[2,3-b]pyridine-5-carboxylic acid, 0.15 ml of triethylamine and 5 ml of dichloromethane is cooled to 0°–5° C. and, under stirring, 0.1 ml of ethyl chlorocarbonate is added dropwise. The reaction is conducted for 20 minutes. Then, following addition of 450 mg of D(—)-α-aminobenzylpenicillin(hereinafter referred as ampicillin) triethylamine salt, the reaction is further conducted at 0°–10° C. for 40 minutes. The dichloromethane is distilled off under reduced pressure at 25° C. and the residue is dissolved by the addition of 5 ml of water and 3 ml of ether. The small amounts of insolubles are filtered off and, under cooling, the water layer is adjusted to pH 2 with 2N-hydrochloric acid. The precipitate is collected by filtration, washed with water and ether, and dried over phosphorus pentoxide. By the above procedure is obtained 428 mg of the desired penicillin as a white powder.

NMR spectrum (DMSO-d$_6$)ppm: 1.42, 1.56(each 3H, s,

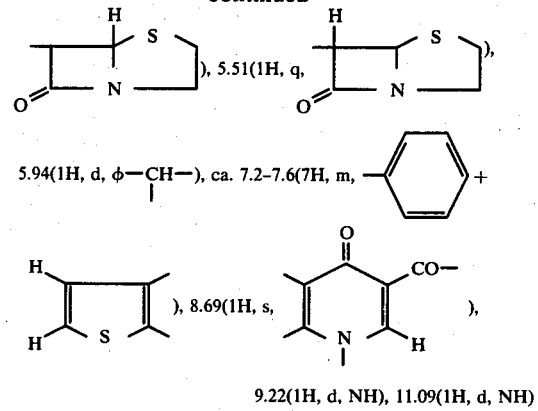

), 5.94(1H, d, φ—CH—), ca. 7.1–7.5(6H, m,

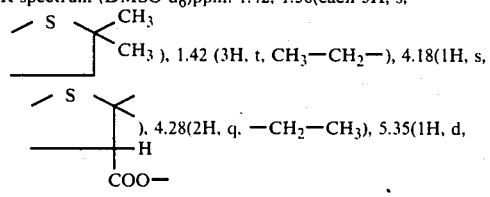

), 9.22(1H, d, NH), 11.14(1H, d, NH).

EXAMPLE 2

D(—)-α-(7-ethyl-4,7-dihydro-2-methyl-4-oxothieno[2,3-b]pyridine-5-carboxamido)benzylpenicillin A mixture of 237 mg of 7-ethyl-4,7-dihydro-2-methyl-4-oxothieno[2,3-b]pyridine-5-carboxylic acid, 0.15 ml of triethylamine and 5 ml of dichloromethane is cooled to 0°–5° C. and, under stirring, 0.1 ml of ethyl chlorocarbonate is added dropwise. The reaction is conducted for 20 minutes. Then, following addition of 450 mg of ampicillin triethylamine salt, the reaction is further conducted for 30 minutes. The dichloromethane is distilled off under reduced pressure at 25° C. and the residue is dissolved in 5 ml of water and 5 ml of ethanol. Under ice-cooling, the water layer is adjusted to pH 2 with 2N-HCl and the resultant crystalline powder is recovered by filtration and washed with water and ether, followed by drying over phosphorus pentoxide. By the above procedure is obtained 531 mg of the desired penicillin which melts at 164°–182° C. (decomp.).

NMR spectrum (DMSO-d$_6$)ppm: 1.42, 1.57(each 3H, s,

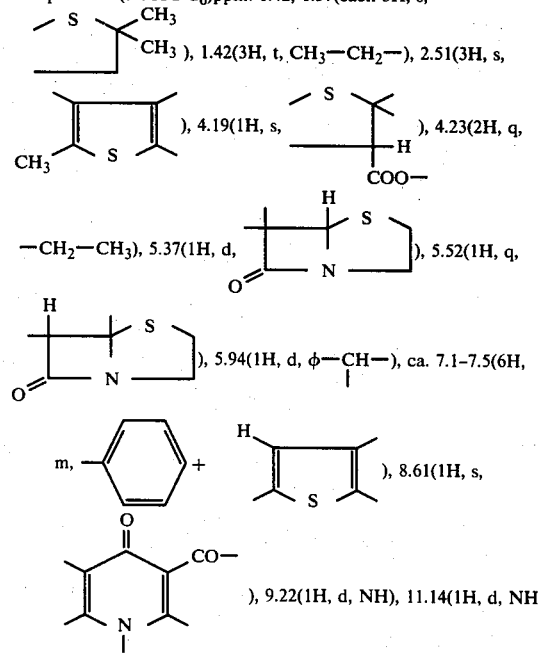

EXAMPLE 3

D(−)-α-(1-ethyl-1,4,5,6,7,8-hexahydro-4-oxo-[I]benzothieno[2,3-b]pyridine-3-carboxamido)benzylpenicillin A mixture of 277 mg of 1-ethyl-1,4,5,6,7,8-hexahydro-4-oxo[I]benzothieno[2,3-b]pyridine-3-carboxylic acid, 0.15 ml of triethylamine and 5 ml of dichloromethane is cooled to 0°-5° C. and, under stirring, 0.1 ml of ethyl chlorocarbonate is added dropwise. The reaction is conducted for 20 minutes. Then, following addition of 450 mg of ampicillin triethylamine salt, the reaction is further conducted at 0°-10° C. with stirring for 30 minutes. The dichloromethane is distilled off under reduced pressure at 25° C. and the residue is dissolved by the addition of 5 ml of water and 3 ml of ether under ice-cooling, the water layer is adjusted to pH 2 with 2N-hydrochloric acid and the resultant crystalline powder is recovered by filtration washed with water and ether, and finally dried over phosphorus pentoxide. By the above procedure is obtained 648 mg of the desired penicillin.

NMR spectrum (DMSO-$d_6$)ppm: 1.39(3H, t, CH$_3$—CH$_2$—), 1.42, 1.56(each 3H, s,  ), 1.76(4H, broad,

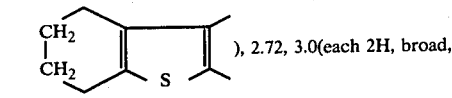 ), 2.72, 3.0(each 2H, broad,

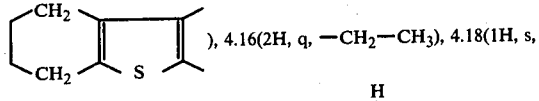 ), 4.16(2H, q, —CH$_2$—CH$_3$), 4.18(1H, s,

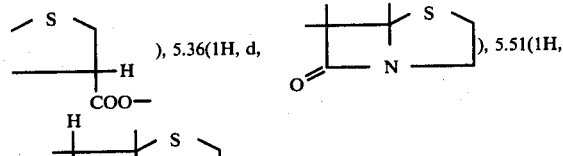 ), 5.36(1H, d,

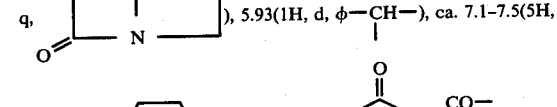), 5.93(1H, d, φ—CH—), ca. 7.1-7.5(5H, m, 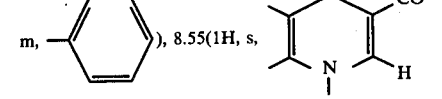), 8.55(1H, s, 9.22(1H, d, NH), 11.07(1H, d, NH)

EXAMPLE 4

D(−)-α-(2-bromo-7-ethyl-4,7-dihydro-4-oxothieno[2,3-b]pyridine-5-carboxamido)benzylpenicillin A mixture of 302 mg of 2-bromo-7-ethyl-4,7-dihydro-4-oxothieno[2,3-b]pyridine-5-carboxylic acid, 0.15 ml of triethylamine and 5 ml of dichloromethane is cooled to 0°-5° C. and, under stirring, 0.1 ml of ethyl chlorocarbonate is added dropwise. Then, following addition of 450 mg of ampicillin triethylamine salt, the mixture is further stirred at 0°-10° C. for 40 minutes. The solvent is distilled off under reduced pressure at 25° C. and the residue is dissolved in water. The small amounts of insolubles are filtered off. To the filtrate is added an equal volume of ethanol and, under ice-cooling, the mixture is adjusted to pH 2 with 2N-hydrochloric acid. The mixture is diluted with water and the resultant crystals are collected by filtration, rinsed with water and dried over phosphorus pentoxide. By the above procedure is obtained 510 mg of the desired penicillin, melting at 167°-170° C.

NMR spectrum (DMSO-$d_6$ + $D_2O$)ppm: 1.41, 1.55(each 3H, s, 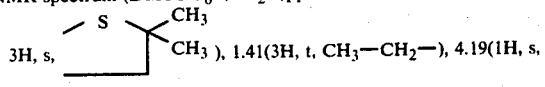 ), 1.41(3H, t, CH$_3$—CH$_2$—), 4.19(1H, s,

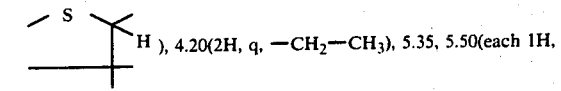 ), 4.20(2H, q, —CH$_2$—CH$_3$), 5.35, 5.50(each 1H,

d, 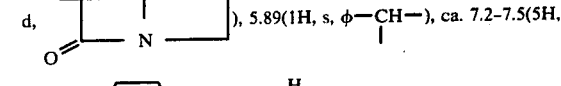 ), 5.89(1H, s, φ—CH—), ca. 7.2-7.5(5H, m, 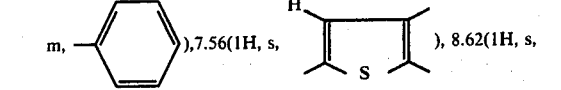),7.56(1H, s,  ), 8.62(1H, s,

 )

EXAMPLE 5

D(−)-α-(2-bromo-4,7-dihydro-4-oxothieno[2,3-b]pyridine-5-carboxamido)benzylpenicillin sodium salt (1) A mixture of 274 mg of 2-bromo-4,7-dihydro-4-oxothieno[2,3-b]pyridine-5-carboxylic acid, 0.3 ml of triethylamine and 10 ml of dichloromethane is cooled to 0°-5° C. and, under stirring, ethyl chlorocarbonate is added dropwise. The reaction is conducted for 30 minutes. Then, following addition of 450 mg of ampicillin triethylamine salt, the reaction is further conducted at 0°-10° C. with stirring for 30 minutes. The dichloromethane is distilled off under reduced pressure and the residue is dissolved by the addition of 10 ml of water and 5 ml of ether. Under ice-cooling, the water layer is adjusted to pH 2 with 2N-HCl. The resultant crystals are collected by filtration, washed with water and ether, and dried. By the above procedure is obtained 600 mg of D(−)-α-(2-bromo-4-ethoxycarbonyloxythieno[2,3-b]pyridine-5-carboxamido)benzylpenicillin, melting at 186°-200° C. (decomp.).

NMR spectrum (DMSO-$d_6$) ppm: 1.42, 1.56(each 3H, s,

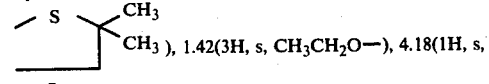 ), 1.42(3H, s, CH$_3$CH$_2$O—), 4.18(1H, s,

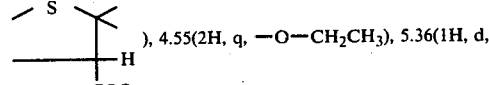 ), 4.55(2H, q, —O—CH$_2$CH$_3$), 5.36(1H, d,

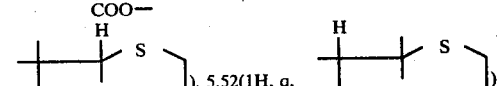

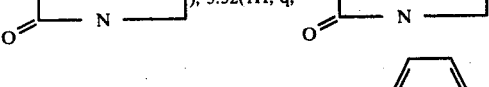), 5.52(1H, q, 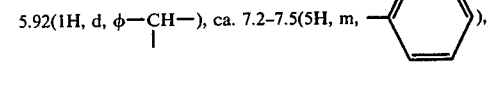), 5.92(1H, d, φ—CH—), ca. 7.2-7.5(5H, m, ⌬ ), -continued 7.58(1H, s, 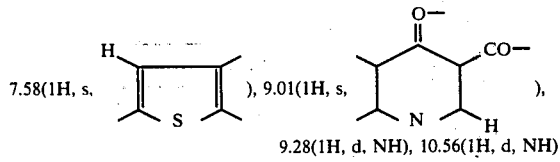), 9.01(1H, s, ), 9.28(1H, d, NH), 10.56(1H, d, NH)

(2) To a mixture of 140 mg of the D(−)-α-(2-bromo-4-ethoxycarbonyloxythieno[2,3-b]pyridine-5-carboxamido)benzylpenicillin obtained above in (1) and 0.5 ml of dimethylformamide is added 0.2 ml or a 2N-solution of sodium 2-ethylhexanoate in isopropyl alcohol, followed by the addition of acetone and ether to the resultant solution. The powdery precipitate is then recovered by filtration, washed with acetone and dried. By the above procedure is obtained 70 mg of the desired compound D(−)-α-(2-bromo-4-hydroxythieno[2,3-b]pyridine-5-carboxamido)benzylpenicillin sodium salt.

NMR spectrum (DMSO-d$_6$)ppm: 1.41, 1.54(each 3H, s,

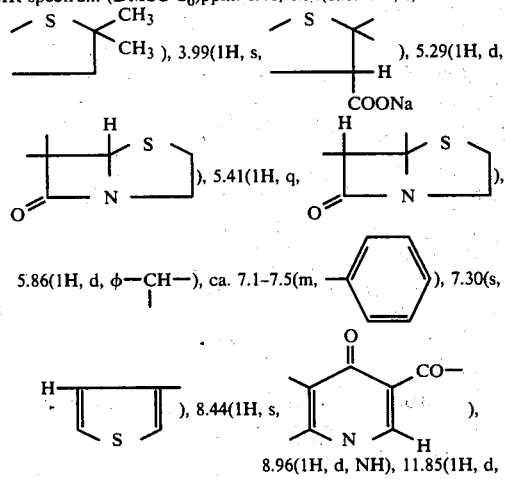

EXAMPLE 6

D(−(-α-(2-chloro-7-ethyl-4,7-dihydro-4-oxothieno[2,3-b]pyridine-5-carboxamido)-p-hydroxybenzylpenicillin A mixture of 420 mg of D(−)-α-amino-p-hydroxybenzylpenicillin (hereinafter reffered as amoxycillin) trihydrate, 3 ml of dichloromethane, 3 ml of dimethylformamide, 0.15 ml of triethylamine and 0.1 g of molecular sieve (type 4A) is stirred at room temperature for 30 minutes to prepare a solution of amoxycillin triethylamine salt. Separately, a mixture of 257 mg of 2-chloro-7-ethyl-4,7-dihydro-4-oxothieno[2,3-b]pyridine-5-carboxylic acid, 0.15 ml of triethylamine and 6 ml of dichloromethane is cooled to 0°–5° C. and, under stirring, 0.1 ml of ethyl chlorocarbonate is added dropwise. The reaction is conducted for 20 minutes. Then, the reaction mixture is added dropwise to the above solution of amoxycillin triethylamine salt at 0°–5° C. with constant stirring. The mixture is further stirred at temperatures not exceeding 10° C. for 1 hour. The reaction mixture is filtered and 50 ml of ice-water is added to the filtrate which is then adjusted to pH 2 with 2N-hydrochloric acid. n-Hexane is added and the resultant precipitate is collected, recrystallized first from a mixture of acetone and water and, then, from a mixture of chloroform, methanol and acetone. By the above procedure is obtained colorless crystals of the desired product. Yield 250 mg; m.p. 224°–229° C. (decomp.)

NMR spectrum (DMSO-d$_6$)ppm: 1.42, 1.57(each 3H, s,

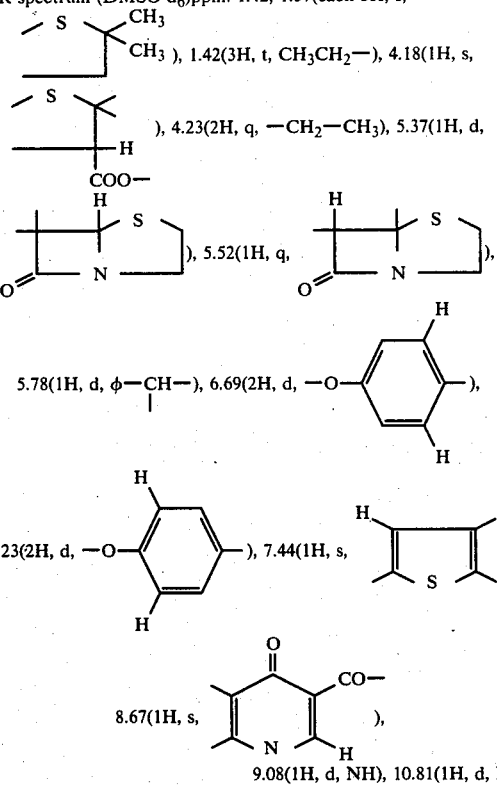

EXAMPLE 7

D(−)-α-(2-bromo-7-ethyl-4,7-dihydro-4-oxothieno[2,3-b]pyridine-5-carboxamido)-p-hydroxybenzylpenicillin sodium salt A mixture of 302 mg of 2-bromo-7-ethyl-4,7-dihydro-4-oxothieno[2,3-b]pyridine-5-carboxylic acid, 12 ml of dichloromethane and 0.15 ml of triethylamine is cooled to 0°–5° C. and, under stirring, 0.1 ml of ethyl chlorocarbonate is added dropwise. The reaction is conducted for 20 minutes. Then, the reaction mixture is added dropwise to an amoxycillin triethylamine salt solution similar to that prepared in Example 6, with cooling and stirring. The reaction is conducted at temperatures not exceeding 10° C. for 1 hour. The reaction mixture is filtered and the filtrate is concentrated under reduced pressure at 25° C. to remove the dichloromethane. The concentrate is diluted with water. The small amounts of insolubles are filtered off and the filtrate is adjusted to pH 2 with 2N-hydrochloric acid. The precipitate is recovereed and dissolved in acetone. To the solution is added a 2N-solution of sodium 2-ethylhexanoate in isopropyl alcohol until white turbidity has disappeared. The precipitate is recovered by filtration, washed with acetone and dried over phosphorus pentoxide under reduced pressure. By this procedure is obtained 580 mg of the desired penicillin as a white powder.

NMR (DMSO-d$_6$)ppm: 1.42, 1.54(each 3H, s,

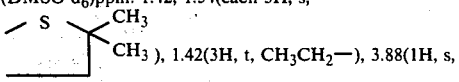

), 4.22(2H, q, —CH$_2$CH$_3$), 5.26(1H, d,

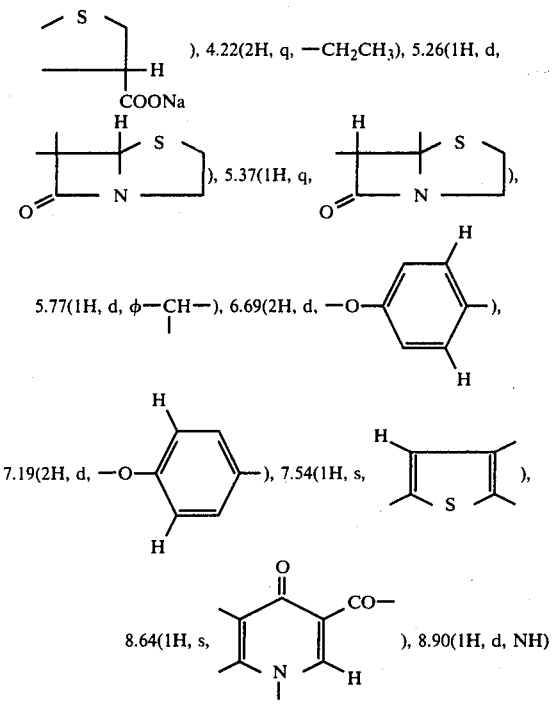

EXAMPLE 8

D(−)-α-(2-bromo-7-ethyl-4,7-dihydro-3-methyl-4-oxo-thieno[2,3-b]pyridine-5-carboxamido)benzylpenicillin sodium salt A mixture of 316 mg of 2-bromo-7-ethyl-4,7-dihydro-3-methyl-4-oxothieno[2,3-b]pyridine-5-carboxylic acid, 6 ml of dichloromethane and 0.15 ml of triethylamine is cooled to 0°–5° C. and, under stirring, 0.1 ml of ethyl chlorocarbonate is added dropwise. The reaction is conducted under cooling for 20 minutes and, following addition of 450 mg of ampicillin triethylamine salt, the mixture is stirred at temperatures not exceeding 10° C. for 1 hour. The solvent is distilled off under reduced pressure at 20° C. and the residue is dissolved by the addition of 5 ml of water and 10 ml of ethanol. The small amounts of insolubles are filtered off and the filtrate is adjusted to pH 2 with 2N-hydrochloric acid and diluted with water. The precipitate is recovered by filtration, rinsed with water and dissolved in acetone. The insolubles are filtered off and a 2N-solution of sodium 2-ethylhexanoate in isopropyl alcohol is added until white turbidity has disappeared. The resultant precipitate is collected by filtration, washed well with acetone and dried over phosphorus pentoxide under reduced pressure. By the above procedure is obtained 450 mg of the desired penicillin as a white powder.

NMR(DMSO-d$_6$)ppm: 1.40, 1.52(each 3H, s,

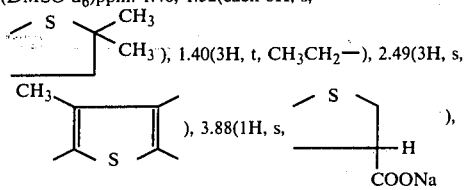

CH$_3$), 1.40(3H, t, CH$_3$CH$_2$—), 2.49(3H, s, 4.18(2H, q, —CH$_2$CH$_3$), 5.25(1H, d,

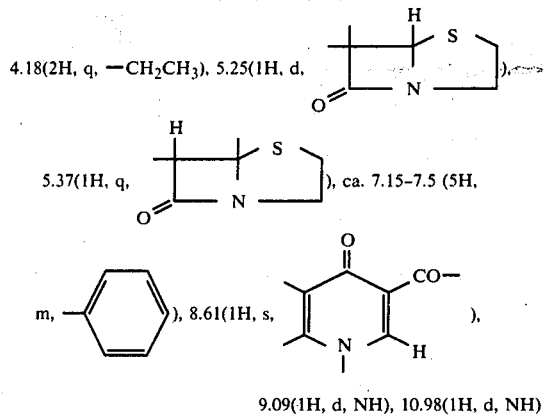

9.09(1H, d, NH), 10.98(1H, d, NH)

EXAMPLE 9

D(−)-α-(4-hydroxy-2-phenylthieno[2,3-b]pyridine-5-carboxamido)benzylpenicillin sodium salt A mixture of 285 mg of 4-hydroxy-2-methyl-3-phenylthieno[2,3-b]pyridine-5-carboxylic acid, 6 ml of dichloromethane and 0.3 ml of triethylamine is cooled to 0°–5° C. and, under stirring, 0.2 ml of ethyl chlorocarbonate is added dropwise. The mixture is further stirred under cooling for 30 minutes. To this solution is added 450 mg of ampicillin triethylamine salt and the mixture is reacted under cooling for 30 minutes. The solvent is then distilled off under reduced pressure at 20° C. and the residue is distributed between dilute hydrochloric acid and chloroform. The chloroform layer is separated, washed with water and then dried over anhydrous sodium sulfate. The solvent is distilled off under reduced pressure at 20° C. The oily residue is dissolved in 1 ml of dimethylformamamide, followed by the addition of 1 ml of a 2N-sodium-2-ethylhexanoate in isopropyl alcohol. After acetone and ether are added, the resultant precipitate is recovered by filtration and dried over phosphorus pentoxide under reduced pressure. By the above procedure is obtained 182 mg of the desired penicillin as a white powder.

NMR (DMSO-d$_6$ + D$_2$O)ppm: 1.40, 1.51(each 3H, s,

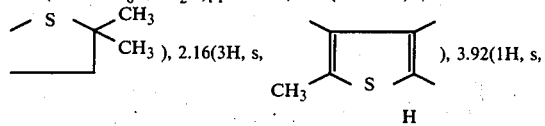

5.34(1H, d,

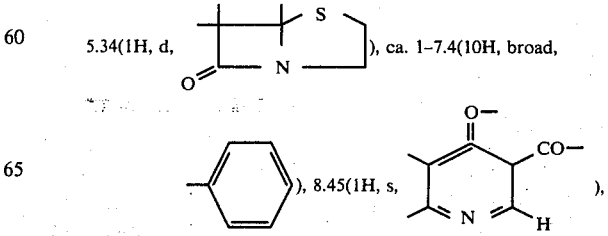

EXAMPLE 10

D(−)-α-(2-benzyl-7-ethyl-4,7-dihydro-4-oxothieno[2,3-b]pyridine-5-carboxamido)benzylpenicillin A mixture of 313 mg of 2-benzyl-7-ethyl-4,7-dihydro-4-oxothieno[2,3-b]pyridine-5-carboxylic acid, 5 ml of dichloromethane and 0.15 ml of triethylamine is cooled to 0°-5° C. and, under stirring, 0.1 ml of ethyl chlorocarbonate is added dropwise. The reaction is further conducted under cooling for 20 minutes and, following addition of 450 mg of ampicillin triethylamine salt, the mixture is stirred at temperatures not exceeding 10° C. for 1 hour. The solvent is distilled off under reduced pressure at 20° C. and the residue is dissolved in aqueous ethanol. The solution is adjusted to pH 2 with 1N-hydrochloric acid under ice-cooling and diluted with water. The resultant crystals are collected by filtration, rinsed with water and dried over phosphorus pentoxide under reduced pressure. By the above procedure is obtained 610 mg of the desired penicillin, melting at 148°-151° C. (decomp.).

NMR (DMSO-d$_6$)ppm: 1.37(3H, t, CH$_3$CH$_2$—), 1.41, 1.56(each 3H, s,

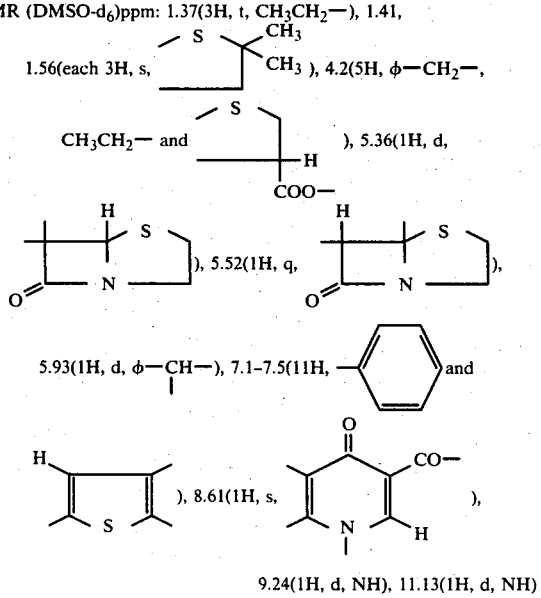

9.24(1H, d, NH), 11.13(1H, d, NH)

EXAMPLE 11

D(−)-α-(2-bromo-4,7-dihydro-7-methyl-4-oxothieno[2,3-b]pyridine-5-carboxamido)benzylpenicillin A mixture of 288 mg of 2-bromo-4,7-dihydro-7-methyl-4-oxothieno[2,3-b]pyridine-5-carboxylic acid, 5 ml of dichloromethane and 0.15 ml of triethylamine is cooled to 0° C. and, under stirring, 0.1 ml of ethyl chlorocarbonate is added dropwise. The resulting solution is stirred for 30 minutes and then 0.45 g of triethylamine salt of ampicillin is added thereto. The mixture is stirred under cooling for 1 hour and then filtered to remove a small amount of insolubles. The solvent is removed in vacuo from the filtrate and the residue is dissolved in about 20 ml of water. After filtration, the filtrate is acidified to about pH 2 with 1N-hydrochloric acid and the resultant pricipitate is collected, washed with water and ethylether and then dried. Yield 360 mg(58%).

NMR (DMSO-d$_6$) δ ppm: 1.43, 1.58(each 3H, s,

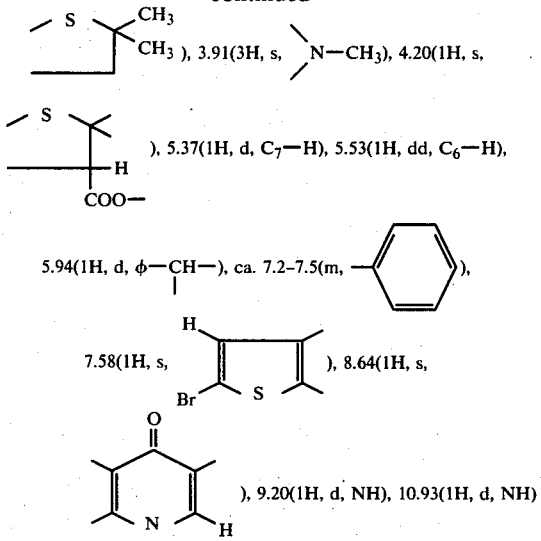

), 9.20(1H, d, NH), 10.93(1H, d, NH)

EXAMPLE 12

7-[D(−)-α-(2-bromo-7-ethyl-4,7-dihydro-4-oxothieno[2,3-b]pyridine-5-carboxamido)-α-phenylacetamido]-3-methyl-3-cephem-4-carboxylic acid A mixture of 302 mg of 2-bromo-7-ethyl-4,7-dihydro-4-oxothieno[2,3-b]pyridine-5-carboxylic acid, 0.15 ml of triethylamine and 5 ml of dichloromethane is cooled with ice-sodium chloride (−5° C.) and, while stirring, 0.1 ml of ethyl chlorocarbonate is added dropwise. The mixture is stirred under cooling for 20 minutes, at the end of which time 0.2 ml of triethylamine and 365 mg of cephalexine hydrate are added. The mixture is stirred under cooling for 30 minutes. The small amounts of insolubles are filtered off and the filtrate is concentrated to dryness under reduced pressure. The residue is dissolved in 10 ml of water and adjusted to pH 2 with 2N-hydrochloric acid. The resultant crystals are collected by filtration, washed with water and n-hexane, and dried over phosphorus pentoxide. Yield 542 mg; m.p. 193°-203° C.

Elemental analysis for C$_{26}$H$_{23}$BrN$_4$O$_6$S$_2$.2H$_2$O. Calcd.: C, 46.78; H, 4.10; N, 8.39. Found: C, 46.86; H, 3.63; N, 8.40.

NMR (DMSO-d$_6$ + D$_2$O)ppm: 1.40(3H, t, CH$_3$CH$_2$—), 1.98(3H, s, —CH$_3$), 3.33(2H, ABq, 4.19(2H, q, —CH$_2$CH$_3$), 4.19(1H, d, 5.59(1H, d, ), 5.83(1H, s, —CH—), ca. 7.2-7.5(5H, m, ), 7.54(1H, s, 8.60(1H, s, 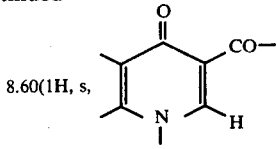 )

EXAMPLE 13

7-[D(—)-α-(2-bromo-7-ethyl-4,7-dihydro-4-oxo-thieno[2,3-b]pyridine-5-carboxamido)-α-phenylacetamido]cephalosporanic acid A mixture of 1.5 g of 2-bromo-7-ethyl-4,7-dihydro-4-oxothieno[2,3-b]pyridine-5-carboxylic acid, 1.5 ml of triethylamine and 50 ml of dichloromethane is cooled to 0° C. and, under stirring, 0.5 ml of ethyl chlorocarbonate is added dropwise. The mixture is further stirred under cooling for 20 minutes, after which 2 g of cephaloglycine is added. The mixture is stirred under cooling for another 30 minutes, at the end of which time the solvent is distilled off under reduced pressure. The residue is dissolved in 50 ml of water and the insolubles are filtered off. The filtrate is adjusted to pH 2 with 1N-hydrochloric acid and the precipitate is recovered by filtration, rinsed with water and dried. Recrystallization from a mixture of chloroform and ethanol gives 2.1 g of colorless crystalline product. The crystals melt at about 193°-about 210° C. (gradually discolored and decomposed). NMR of this product indicates that it includes a half-molecule of crystalline ethanol.

NMR(DMSO-d$_6$ + D$_2$O)ppm: 1.10(1.5H, t, ½CH$_3$CH$_2$OH), 1.46(3H, t, CH$_3$CH$_2$N), 2.04(3H, s, CH$_3$—CO—), 3.49(3H,

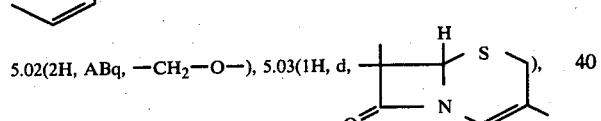

H + ½CH$_3$CH$_2$OH), 4.27(2H, q, CH$_3$CH$_2$N<), 4.68, 5.02(2H, ABq, —CH$_2$—O—), 5.03(1H, d, 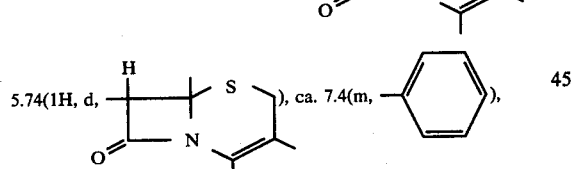

5.74(1H, d, 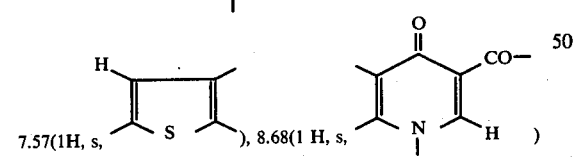 ), ca. 7.4(m, ), 7.57(1H, s, ), 8.68(1 H, s, )

EXAMPLE 14

7-[D(—)-α-(2-bromo-7-ethyl-4,7-dihydro-4-oxo-thieno[2,3-b]pyridine-5-carboxamido)-α-phenylacetamido]-3-(1-methyl-1H-tetrazol-5-ylthiomethyl)-3-cephem-4-carboxylic acid A mixture of 151 mg of 4-oxothieno[2,3-b]pyridine-5-carboxylic acid, 0.15 ml of triethylamine and 5 ml of dichloromethane is cooled to a temperature below 0° C. and, under stirring, 0.05 ml of ethyl chlorocarbonate is added. The mixture is stirred under cooling for 20 minutes, after which 230 mg of 7-(D(—)-α-amino-α-phenylacetamido)-3-(1-methyl-1H-tetrazol-5-ylthiomethyl)-3-cephem-4-carboxylic acid is added. This mixture is further stirred under ice-cooling for 40 minutes and, then the solvent is distilled off under reduced pressure. The residue is dissolved in 6 ml of water and the solution is adjusted to pH 2 with hydrochloric acid. The resultant precipitate is recovered by filtration, rinsed with water and dried over phosphorus pentoxide. By the above procedure is obtained 325 mg of the desired compound.

NMR(DMSO-d$_6$ + D$_2$O)ppm: 1.45(3H, t, CH$_3$CH$_2$—), 3.65(2H, broad, 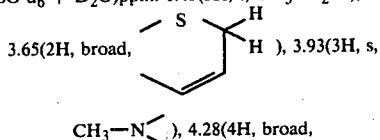 ), 3.93(3H, s, CH$_3$—N< ), 4.28(4H, broad, —CH$_2$CH$_3$ + —CH$_2$—S—), 5.0(1H, d, 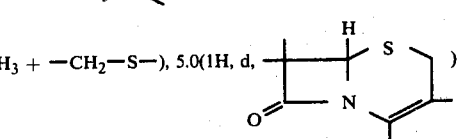 ), 5.73(1H, d, 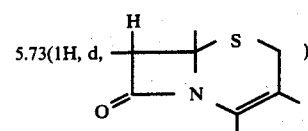 ), 5.84(1H, s, φ—CH—), 7.4(5H, m, ), 7.60(1H, s, 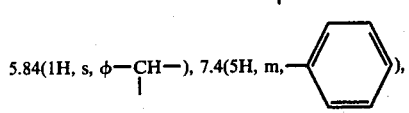 ), 8.67(1H, s, 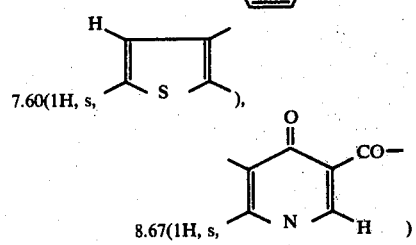 )

EXAMPLE 15

7-[D(—)-α-(2-bromo-4,7-dihydro-7-methyl-4-oxo-thieno[2,3-b]pyridine-5-carboxamido)-phenylacetamido]-3-(1-methyl-1H-tetrazol-5-ylthiomethyl)-3-cephem-4-carboxylic acid A mixture of 144 mg of 2-bromo-4,7-dihydro-7-methyl-4-oxothieno[2,3-b]pyridine-5-carboxylic acid, 0.15 ml of triethylamine and 5 ml of dichloromethane is cooled to a temperature below 0° C. and, under stirring, 0.05 ml of ethyl chlorocarbonate is added. The mixture is stirred under cooling for 30 minutes, after which 230 mg of 7-(D(—)-α-amino-α-phenylacetamido)-3-(1-methyl-1H-tetrazol-5-ylthiomethyl)-3-cephem-4-carboxylic acid is added. The mixture is further stirred under cooling for one hour. The small amounts of insolubles are filtered off and the filtrate is concentrated to dryness under reduced pressure. The residue is diluted with 10 ml of water and, under ice-cooling and stirring, adjusted to pH 2 with 1N-hydrochloric acid. The mixture is further stirred for a short time. The insoluble white powder is collected by filtration, washed with water, ethanol and ether and finally dried. By the above procedure is obtained 294 mg of the desired compound.

NMR(DMSO-d₆)ppm: 3.60(2H, [structure]), 3.92, 3.94(each 3H, s, 2 x CH₃—N<), 4.27(2H, —CH₂—S—), 5.01(1H, d, [structure]), 5.73(1H, q, [structure]), 5.88(1H, d, φ—CH—), ca. 7.25–7.55(5H, m, [phenyl]), 7.62(1H, s, [thiophene structure]), 8.65(1H, s,

[pyridone-CO— structure]), 9.40(1H, d, NH), 10.97(1H, d, NH)

What we claim is:

1. A thienopyridine of the formula:

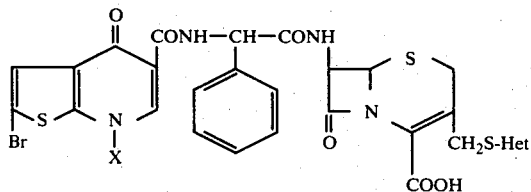

wherein X is methyl or ethyl and Het is an unsubstituted or substituted nitrogen-containing heterocyclic group; the nitrogen-containing heterocyclic group being selected from the group consisting of pyridyl, N-oxide-pyridyl, pyrimidyl, pyridazinyl, N-oxide-pyridazinyl, pyrazolyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-thiazolyl, 1H-tetrazolyl and 2H-tetrazolyl, the substituent on the substituted nitrogen-containing heterocyclic group being selected from the group consisting of alkyl group having from 1 to 3 carbon atoms, alkoxy group having 1 to 3 carbon atoms, halogen, a halogenalkyl group having from 1 to 3 carbon atoms, hydroxyl, mercapto, amino, carboxyl, carbamoyl, morpholino, sulfo, alkoxycarbonyl having from 1 to 4 carbon atoms, mono-, di- or tri-$C_{1-3}$ alkyl amino $C_{1-3}$ alkyl, mono-, and di-$C_{1-3}$ alkylcarbonyl $C_{1-3}$ alkyl, alkylthioalkyl group having 1 to 3 carbon atoms in the alkyl groups, $C_{1-3}$ alkylthio, and $C_{1-3}$ alkylamino group, or a pharmaceutically acceptable salt thereof.

2. A thienopyridine according to claim 1, wherein the nitrogen-containing heterocyclic group is triazolyl, tetrazolyl or thiadiazolyl.

3. A thienopyridine according to claim 1, wherein the nitrogen-containing heterocyclic group is triazolyl, tetrazolyl or thiadiazolyl group which is substituted.

4. 7-[D-α-(2-bromo-7-ethyl-4,7-dihydro-4-oxo-thieno[2,3-b]pyridine-5-carboxamido)-α-phenylacetamido]-3-(1-methyl-1H-tetrazol-5-ylthiomethyl)-3-cephem-4-carboxylic acid.

5. 7-[D-α-(2-bromo-4,7-dihydro-7-methyl-4-oxo-thieno[2,3-b]pyridine-5-carboxamido)-α-phenylacetamido]-3-(1-methyl-1H-tetrazol-5-ylthiomethyl)-3-cephem-4-carboxylic acid.

6. An anti-bacterially effective pharmaceutical composition comprising a thienopyridine according to claim 1, together with pharmaceutically acceptable carrier or diluent therefor.

* * * * *